United States Patent [19]

Braquet et al.

[11] Patent Number: 5,019,576

[45] Date of Patent: May 28, 1991

[54] 2-SUBSTITUTED N,N'-DITRIMETHOXYBENZOYL PIPERAZINES AND THERAPEUTIC COMPOSITIONS CONTAINING THEM

[75] Inventors: Pierre Braquet, Garches; Eduardo Pirotzky, Paris; Jean-Jacques Godfroid, Paris; Francoise Heymans, Paris, all of France

[73] Assignee: Societe de Conseils de Recherches et d'Applications Scientifiques (S.C.R.A.S.), France

[21] Appl. No.: 506,421

[22] Filed: Apr. 9, 1990

[30] Foreign Application Priority Data

Apr. 15, 1989 [GB] United Kingdom ................. 8908587

[51] Int. Cl.$^5$ ..................... A61B 31/495; C07D 41/04
[52] U.S. Cl. ..................................... 514/255; 544/387
[58] Field of Search ......................... 544/387; 514/255

[56] References Cited

FOREIGN PATENT DOCUMENTS 0368670 5/1990 European Pat. Off. ............ 544/387

*Primary Examiner*—Frederick E. Waddell
*Assistant Examiner*—James H. Turnipseed
*Attorney, Agent, or Firm*—Lucas & Just

[57] ABSTRACT

This invention relates to piperazine derivatives of the general formula I

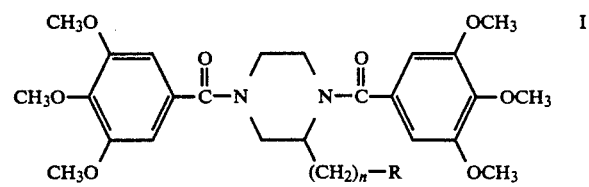

wherein —$(CH_2)_n$— represents a straight or branched chain alkyl group having from n=1 to n=20 carbon atoms, and R represents a hydrogen atom, a branched alkyl group, a cycloalkyl group having from 5 to 10 carbon atoms, a phenyl group, optionally substituted by one or several chlorine atoms, methyl or methoxy groups, or straight or branched chain alkenyl groups having from 3 to 11 carbon atoms, to a preparation process of said compounds and to therapeutic compositions containing them as an active ingredient.

2 Claims, No Drawings

2-SUBSTITUTED N,N'-DITRIMETHOXYBENZOYL PIPERAZINES AND THERAPEUTIC COMPOSITIONS CONTAINING THEM

The present invention relates to piperazine derivatives of the general formula I

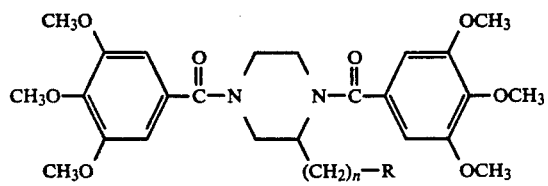

wherein

—$(CH_2)_n$— represents a straight or branched chain alkyl group having from $n=1$ to $n=20$ carbon atoms, and R represents a hydrogen atom, a branched alkyl group, a cycloalkyl group having from 5 to 10 carbon atoms, a phenyl group, optionally substituted by one or several chlorine atoms, methyl or methoxy groups, or straight or branched chain alkenyl groups having from 3 to 11 carbon atoms, and to pharmaceutically acceptable salts thereof.

In the European patent EP 284 359 are disclosed 1,4-substituted piperazines with a 3,4,5-(trimethoxy) benzoyl group but only one of the substituents is a 3,4,5-(trimethoxy)benzoyl group, the other one being a condensed polycyclic carbonyl group.

The present invention relates to 1,2,4-substituted piperazine compounds which present a 1,4-bis-substitution by a 3,4,5-(trimethoxy)benzoyl group. This serie of new piperazine derivatives is prepared in few steps and provides greater pharmaceutical activities than the 1,4-substituted piperazines of the prior art.

This invention also relates to a preparation process of the compounds of the general formula I, which process comprises reacting a compound of the general formula R—$(CH_2)_{n-1}$—X wherein R and n are as above defined and X is a bromine or a chlorine atom with pyrazylmethyl sodium. Pyrazylmethyl sodium may be prepared from methylpyrazine and sodium amide in liquid ammonia. The reaction is suitably carried out in a mixture of liquid ammonia diethyl ether at −50° C. (dry ice cooling).

The resulting substituted methylpyrazine of the general formula II

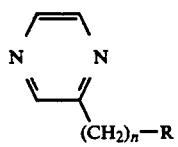

is then reduced either with hydrogen over a palladium (10%) on charcoal catalyst (in ethanol) or by sodium in ethanol (the latter being preferred when R is unsaturated) leading to the substituted piperazine of the general formula III

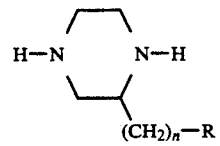

which on acylation by treatment with 3,4,5-trimethoxybenzoyl chloride in benzene, in the presence of triethylamine, at room temperature, gives the final product of the general formula I.

The invention relates, finally, to therapeutic compositions of matter containing one of the compounds I, as an active ingredient therein.

EXAMPLE 1

N,N'-bis-(3',4',5'-trimethoxybenzoyl)-2-n-octyl piperazine R=H, n=8

Step a

Preparation of n-octyl pyrazine (Compound II in which R=H and n=8)

To 15.6 g (0.4 mole) of sodium amide in 400 ml of anhydrous liquid ammonia cooled at −50° C., there were added 37.6 g (0.4 mole) of methyl pyrazine. The mixture was stirred for half an hour at the same temperature.

Then, n-heptyl bromide (35.8 g, 0.2 mole), diluted with an equal volume of anhydrous diethyl ether, was added over a 20 minutes period and the mixture was stirred for an additional hour. The reaction was quenched by the addition of 25 g of solid ammonium chloride and the ammonia was replaced by diethyl ether. The mixture was heated until the diethyl ether just started to reflux, and was then poured into ice, rendered strongly acidic by the addition of concentrated HCl and extracted with diethyl ether. The aqueous layer was then rendered basic by the addition of NaOH and extracted with $CHCl_3$.

After drying over $MgSO_4$ and filtration, the evaporation of the organic phase led to a residue which was chromatographed on a silica gel column using diethyl ether/petroleum ether (15:85, v:v) as eluent.

The title compound II (33.4 g, yield 87%) was recovered as a pale yellow liquid.

IR (film): 3050 (aromatic C-H), 2940, 2860 (C-H), 1580, 1525 (aromatic ring) $cm^{-1}$.

$^1H$ NMR (60 MHz, $CDCl_3$, HMDS) δ ppm: 8.5 (large s, 3H, aromatic H), 2.75 (t, 2H, $CH_2$-C=N), 1.7 (m, 2H, $CH_2$-C-C=N), 1.25 (large s, 10H, $(CH_2)_5$), 0.8 (t, 3H, $CH_3$).

Step b

Preparation of 2-n-octyl piperazine (Compound III in which R=H and n=8).

A solution of 3.4 g (20 mmoles) of the compound II, prepared in step (a) above and 50 mg Pd (10%)/ charcoal in 100 ml ethanol was treated with $H_2$ under a pressure of 2.8 bars under stirring for 3 hours at room temperature. After filtration and evaporation of the ethanol, the title compound was recovered with a 100% yield as a very hygroscopic solid.

IR (in paraffin oil): 3240 (N—H), 2920, 2850 (C—H) $cm^{-1}$.

Step c

Preparation of
N,N'-bis-(3',4',5'-trimethoxybenzoyl)-2-noctyl
piperazine (Compound I in which R=H and n=8)

A solution of 3 g (15 mmoles) of the compound III prepared in step (b) above in 30 ml of dry benzene and 1.5 ml of $(C_2H_5)_3N$ was added dropwise to a solution of 7.6 g (33 mmoles) of 3,4,5-trimethoxybenzoyl chloride in 30 ml of dry benzene. The mixture was stirred overnight at room temperature. Then, the excess of acyl chloride was decomposed by the addition of 2 ml of ethanol whilst stirring for a 1 hour at room temperature. $H_2O$ was added and the organic layer was washed with a 5% solution of $NaHCO_3$, then with $H_2O$.

After drying over $MgSO_4$ and evaporation of the solvent, a purification on a silica gel column using $CHCl_3$ then $MeOH/CHCl_3$ (0.5:99.5, v:v) gave 6.5 g (yield 74%) of the title compound as white crystals; m.p.: 174° C.

IR (in paraffin oil): 2930, 2850 (C-H), 1625 (C=O), 1585 (Ar C=C) $cm^{-1}$.

$^1H$ NMR (80 MHz, $CDCl_3$, HMDS) δ ppm: 6.56 (s, 4H, Ar H), 4.62-3.87 (m, 4H, $CH_2NCO$), 3.81 (large s, 18H, $CH_3O$), 3.4-2.7 (m, 3H, $CH_2NCO+CHNCO$), 1.73-1.4 (m, 2H, $RCH_2$-C-NCO), 1.16 (large s, 12H, $(CH_2)_6$) 0.8 (t, 3H, $CH_3$).

EXAMPLE 2

N,N'-bis-(3',4',5'-trimethoxybenzoyl)
2-(3'',3''-dimethyl) -butyl piperazine R=-C(CH_3)_3, n=2

Step a

Preparation of (3,3-dimethyl)-butyl pyrazine
(Compound II in which R=H, n=6 and
$-(CH_2)_6H=-(CH_2)_2 C(CH_3)_3$)

Proceeding as described in example 1 step (a) but starting with neopentyl bromide instead of the n-heptyl bromide, the title compound was recovered as a liquid.

IR (film): 3050 (aromatic C-H), 2940, 2860 (C-H), 1580, 1525 (aromatic ring) $cm^{-1}$.

$^1HNMR$ (80 MHz, $CDCl_3$, HMDS) δ ppm: 8.43 (large s, 3H, aromatic H), 2.73 (m, 2H, $CH_2$-C=N), 1.55 (m, 2H, $CH_2$-C-C=N), 0.92 (s, 3H, $CH_3$).

Step b

Preparation of 2-(3',3,-dimethyl)-butyl piperazine
(Compound III in which R=H, n=6 and
$-(CH_2)_6H=-(CH_2)_2 C(CH_3)_3$).

To a solution of 6.5 g (40 mmoles) of the compound II prepared in step (a) above in 200 ml of absolute ethanol, there were added in small portions and over a period of 1 hour 9.2 g (44 mmoles) of sodium and the mixture was stirred for an additional hour. The mixture was then poured into ice, extracted with $CHCl_3$, washed with water and dried over $Na_2SO_4$. The evaporation of the solvent led to a crude residue which was used as such in the next step.

Step c

Preparation of N,N'-bis-(3',4',5'-trimethoxybenzoyl) 2-(3'',3''-dimethyl)-butyl piperazine (Compound I in which R=H, n=6 and $-(CH_2)_6H=-(CH_2)_2 C(CH_3)_3$).

This step was conducted as in example 1, step (c). The title compound was recovered as a wax.

IR (film): 2930, 2850 (C-H), 1625 (C=O), 1585 (Ar C=C) $cm^{-1}$.

$^1H$ NMR (80 MHz, $CDCl_3$, HMDS) δ ppm: 6.58 (d, 4H, Ar H), 4.5-3.95 (m, 2H, $CH_2NCO$), 3.81 (s, 18H, $CH_3O$), 3.37-2.65 (m, 5H, $CH_2NCO$ and CHNCO), 1.57 (m, 2H, $CH_2$-C-NCO), 1.31-1.00 (m, 2H, $CH_2CMe_3$), 0.82 (s, 9H, $CH_3$).

EXAMPLE 3

N,N'-bis-(3',4',5'-trimethoxybenzoyl) 2-methyl
piperazine R=H, n=1

Step a and b

Commercial 2-methyl piperazine

Step c

Proceeding as described in example 1, step (c), the title compound cas recovered as a white powder; m.p.: 176°-177° C.

IR (in paraffin oil): the same as for example 1.

$^1H$ NMR (80 MHz, $CDCl_3$, HMDS) δ ppm: 6.65 (d, 4H, ArH), 4.60-4.12 (m, 3H, $CH_2NCO+CHNCO$), 3.77 (large s, 18H, $CH_3O$), 3.57-2.75 (m, 4H, $CH_2NCO$), 1.27 (d, 3H, $CH_3$).

EXAMPLE 4

N,N'-bis-(3',4',5'-trimethoxybenzoyl) 2-n-pentyl
piperazine

Proceeding as described in example 1 steps (a), (b), (c), but starting with n-butyl bromide instead of the n-heptyl bromide, the title compound was recovered as white crystals; m.p.: 139°-140° C.

IR (in paraffin oil): 2925, 2850 (C-H), 1620 (C=O), 1580 (Ar C=C) $cm^{-1}$.

$^1HH$ NMR (80 MHz, $CDCl_3$, HMDS) δ ppm: 6.53 (d, 4H, Ar H), 4.48-3.92 (m, 3H, $CH_2NCO+CHNCO$), 3.81 (large s, 18H, $CH_3O$), 3.6-2.68 (m, 4H, $CH_2NCO$), 1.75-1.37 (m, 2H, $CH_2$-C-NCO), 1.12 (large s, 6H, $(CH_2)_3$), 0.77 (t, 3H, $CH_3$).

EXAMPLE 5

N,N'-bis-(3',4',5'-trimethoxybenzoyl) 2-n-pentadecyl
piperazine R=H, n=15

Proceeding as described in example 1 steps (a), (b), (c), but starting with n-tetradecanyl bromide instead of the n-heptyl bromide, the title compound was recovered as a white powder; m.p.: 68° C.

IR (in paraffin oil): the same as the compound described in example 1.

$^1H$ NMR (80 MHz, $CDCl_3$, HMDS) δ ppm: 6.56 (d, 4H, Ar H), 4.47-3.90 (m, 3H, $CH_2NCO+CHNCO$), 3.80 (large s, 18H, $CH_3O$), 3.40-2.87 (m, 4H, $CH_2NCO$), 1.85-1.40 (m, 2H, $CH_2$-C-NCO), 1.17 (large s, 26H, $(CH_2)_{13}$), 0.82 (t, 3H, $CH_3$).

EXAMPLE 6

N,N'-bis-(3',4',5'-trimethoxybenzoyl) 2-n-nonadecyl
piperazine R=H, n=19

Proceeding as described in example 1, steps (a), (b), (c), but starting with n-octadecyl bromide instead of the n-heptyl bromide, the title compound was recovered as a white powder; m.p.: 76° C.

IR (in paraffin oil): the same as the compound described in example 1.

$^1$ NMR (80 MHz, $CDCl_3$, HMDS) δ ppm: 6.51 (d, 4H, Ar H), 4.61-4.10 (m, 3H, $CH_2NCO+CHNCO$), 3.85 (large s, 18H, $CH_3O$), 3.45-2.90 (m, 4H, $CH_2NCO$), 1.85–1.47 (m, 2H, CH$_2$-C-NCO), 1.22 (large s, 34H, (CH$_2$)$_{17}$), 0.83 (t, 3H, CH$_3$).

EXAMPLE 7

N,N'-bis-(3',4',5'-trimethoxybenzoyl)-2-n-(cyclohexylethyl) piperazine

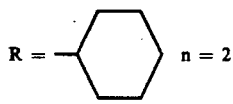

Proceeding as described in example 1, steps (a), (b) and (c), but starting with cyclohexylmethyl bromide instead of the n-heptyl bromide ; the title compound was recovered as a white powder; m.p.: 123°–125° C.

IR: the same as for example 1.

$^1$H NMR (80 MHz, CDCl$_3$, HMDS) δ ppm: 6.52 (d, 4H, ArH), 4.60–4.10 (m, 3H, CH$_2$NCO+CHNCO), 3.80 (large s, 18H, CH$_3$O), 3.50–2.77 (m, 4H, CH$_2$NCO), 1.84–1.40 (m, 3H,

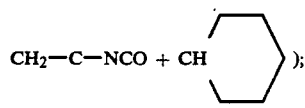

1.22 (large s, 12H, CH$_2$-cyclohexyl +CH$_2$ of the cyclohexyl).

EXAMPLE 8

N,N'-bis-(3',4',5'-trimethoxybenzoyl)-2-n-(3,4,5-(trimethoxy)phenethyl) piperazine

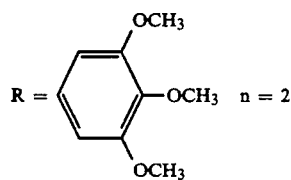

Proceeding as described in example 2, steps (a), (b) and (c), but starting with 3,4,5-(trimethoxy)benzyl chloride instead of the n-heptyl bromide; the title compound was recovered as white crystals; m.p.: 117°–121° C.

IR (in paraffin oil): 3060, 3015, 3000 (aromatic C-H), 2940, 2860 (C-H), 1630 (C=O), 1585 (ArC=C)cm$^{-1}$.

$^1$H NMR (80 MHz, CDCl$_3$, HMDS) δ ppm: 6.60 (large s, 6H, ARH), 4.60–4.12 (m, 3H, CH$_2$NCO+CHNCO), 3.80 (large s, 27H, CH$_3$O), 3.50–2.40 (m, 6H, CH$_2$NCO+CH$_2$φ(OMe)$_3$), 1.70 (m, 2H, CH$_2$-C-NCO).

EXAMPLE 9

N,N'-bis-(3',4',5'-trimethoxybenzoyl)-2-n-(benzyl) piperazine

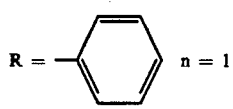

Proceeding as described in example 1, steps (a), (b) and (c), but starting with phenyl bromide instead of the n-heptyl bromide; the title compound was recovered as a white powder; m.p.: 168°–170° C.

IR: the same as for example 8.

$^1$H NMR: (80 MHz, CDCl$_3$, HMDS) δ ppm: 7.24 (large s, 5H, C$_6$H$_5$), 6.55 (d, 4H, trimethoxyphenyl ArH), 4.58–4.10 (m, 3H, CH$_2$NCO+CHNCO), 3.80 (large s, 18H, CH$_3$O), 3.50–2.72 (m, 6H, CH$_2$NCO+CH$_2$φ).

EXAMPLE 10

N,N'-bis-(3',4',5'-trimethoxybenzoyl)-2-n-(phenethyl) piperazine

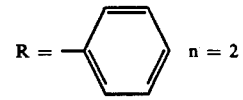

Proceeding as described in example 2, steps (a), (b) and (c), but starting with benzyl bromide instead of the n-heptyl bromide; the title compound was recovered as a white powder; m.p.: 153°–156° C.

IR: the same as for example 8.

$^1$H NMR (80 MHz, CDCl$_3$, HMDS) δ ppm: 7.25 (large s, 5H, C$_6$H$_5$), 6.58 (d, 4H, trimethoxyphenyl ArH), 4.60–4.10 (m, 3H, CH$_2$NCO+CHNCO), 3.80 (large s, 18H, CH$_3$O), 3.50–2.70 (m, 6H, CH$_2$NCO+CH$_2$φ), 2.03 (m, 2H, CH$_2$-C-NCO).

EXAMPLE 11

N,N'-bis-(3',4',5'-trimethoxybenzoyl)-2-n-(phenyl-n-propyl) piperazine

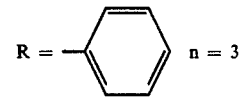

Proceeding as described in example 2, steps (a), (b) and (c), but starting with (phenethyl)bromide instead of the n-heptyl bromide; the title compound was recovered as crystals; m.p.: 133°–135° C.

IR: the same as for example 8.

$^1$H NMR (80 MHz, CDCl$_3$, HMDS) δ ppm: 7.22 (large s, 5H, C$_6$H$_5$), 6.55 (d, 4H, trimethoxyphenyl ArH), 4.56–4.10 (m, 3H, CH$_2$NCO+CHNCO), 3.78 (large s, 18H, CH$_3$O), 3.47–2.70 (m, 6H, CH$_2$NCO+CH$_2$φ), 1.80–1.45 (m, 4H, CH$_2$-C-NCO+CH$_2$-C-φ).

EXAMPLE 12

N,N'-bis-(3',4',5'-trimethoxybenzoyl)-2-n-(p-(methoxy) phenethyl) piperazine

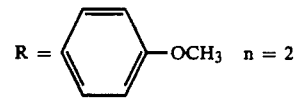

Proceeding as described in example 2, steps (a), (b) and (c), but starting with p-(methoxy)benzyl chloride instead of the n-heptyl bromide; the title compound was recovered as crystals; m.p.: 99°–103° C.

IR: the same as for example 8.

$^1$H NMR (80 MHz, CDCl$_3$, HMDS) δ ppm: 7.09 (d, 2H, ortho mono methoxyphenyl ArH), 6.80 (d, 2H, meta monomethoxyphenyl ArH), 6.60 (d, 4H, trimethoxybenzoyl ArH), 4.60–4.08 (m, 3H, CH₂NCO+CH-NCO), 3.78 (large s, 21H, CH₃O), 3.45–2.60 (m, 6H, CH₂NCO+CH₂φOMe), 1.92 (m, 2H, CH₂-C-NCO).

EXAMPLE 13

N,N'-bis-(3',4',5'-trimethoxybenzoyl)-2-n-(p-(methyl) phenylpropyl) piperazine

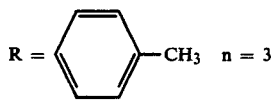

Proceeding as described in example 2, steps (a), (b) and (c), but starting with p-(methyl)phenethyl bromide instead of the n-heptyl bromide; the title compound was recovered as white crystals; m.p.: 83°–85° C.

IR: the same as for example 8.

¹H NMR (80 MHz, CDCl₃, HMDS) δ ppm: 7.10 (s, 4H, methylphenyl ArH), 6.58 (d, 4H, trimethoxybenzoyl ArH) 4.55–4.12 (m, 3H, CH₂NCO+CHNCO), 3.80 (large s, 18H, CH₃O), 3.45–2.68 (m, 6H, CH₂NCO+CH₂φMe), 2.33 (s, 3H, CH₃φ), 1.82–1.44 (m, 4H, CH₂-C-NCO+CH₂-C-φMe).

EXAMPLE 14

N,N'-bis-(3',4',5'-trimethoxybenzoyl)-2-n-(p-(chloro) phenethyl) piperazine

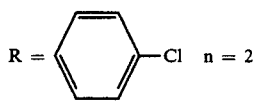

Proceeding as described in example 2, steps (a), (b) and (c), but starting with 4-chlorobenzyl chloride, the title compound was recovered as crystals m.p.: 92°–93° C.

IR: the same as for example 8.

¹H NMR (80 MHz, CDCl₃, HMDS) δ ppm: 7.38 (s, 4H, p-chlorophenyl ArH), 6.60 (d, 4H, trimethoxyphenyl ArH), 4.60–4.10 (m, 3H, CH₂NCO+CHNCO), 3.78 (large s, 18H, CH₃O), 3.52–2.65 (m, 6H, CH₂NCO+CH₂φCl), 2.0 (m, 2H, CH₂-C-NCO).

EXAMPLE 15

N,N'-bis-(3',4',5,-trimethoxybenzoyl)-2-n-(2,3-(dichloro) phenethyl) piperazine

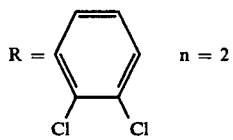

Proceeding as described in example 2, steps (a), (b) and (c), but starting with 2,3-(dichloro)benzyl bromide instead of the n-heptyl bromide; the title compound was recovered as crystals; m.p.: 108°–110° C.

IR (in paraffin oil): the same as for example 8.

¹H NMR (80 MHz, CDCl₃, HMDS) δ ppm: 7.38 (m, 3H, C₆H₃), 6.60 (d, 4H, trimethoxyphenyl ArH), 4.55–4.12 (m, 3H, CH₂NCO+CHNCO), 3.82 (large s, 18H, CH₃O), 3.55–2.65 (m, 6H, CH₂NCO+CH₂φCl₂), 2.03 (m, 2H, CH₂-C-NCO).

EXAMPLE 16

N,N'-bis-(3',4',5'-trimethoxybenzoyl)-2-n-(p-(allyl) phenethyl) piperazine

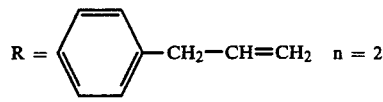

Proceeding as described in example 1, steps (a), (b) and (c), but starting with p-(allyl)benzyl bromide instead of the n-heptyl bromide; the title compound was recovered as a white powder; m.p.: 111°–114° C.

IR (in paraffin oil): 3080 (=C-H), 3060, 3030, 3000 (ArC-H), 1640 (C=O and C=C), 1585 (ArC=C)cm ¹H NMR (80 MHz, CDCl₃, HMDS) δ ppm: 7.12 (s, 4H, C₆H₄), 6.58 (d, 4H, trimethoxyphenyl ArH), 5.94 (m, 1H, CH=), 5.05 (m, 2H, =CH₂), 4.50–4.10 (m, 3H, CH₂NCO+CHNCO), 3.81 (large s, 18H, CH₃O), 3.50–2.63 (m, 8H, CH₂NCO+CH₂φCH₂), 2.0 (m, 2H, CH₂-C-NCO).

TOXICOLOGY

The compound of the invention has been administered to mice for determination of acute LD₅₀. For all the compounds of the invention, LD₅₀ was over 600 mg/kg.

PHARMACOLOGY

A proof of the pharmaceutical interest of the compounds of the invention has been established by the following pharmaceutical experimentation:

1. —Inhibition of the platelets aggregation on New Zealand Rabbits

The derivatives of the present invention revealed an interesting PAF-antagonist activity with respect to platelet aggregation induced by 2.5 nm of PAF on platelet rich plasma (PRP) according to Born method.

This activity was evidenced by binding studies on a rabbit platelet homogenate. In this preparation indeed, those derivatives inhibit the specific bond of ³[H]—PAF, whereas they are without significative effect on the binding of the appropriate ligands on tissue homogenates rich in benzodiazepinic (central and peripheral), histaminergic (H₁ and H₂) and adrenergic (α₁, α₂, β₂, β₃) receptors, to angiotensine II or to ANF. Their affinity is therefore characteristic of PAF receptors.

The experimentation was conducted on platelets with plasma of New Zealand rabbits.

Blood samples were taken from auricular artery and placed in a citrate buffer (3.8%; pH 7.4); blood was further centrifugated for 15 mn at 1200 rpm.

The tested sample was prepared in DMSO, then poured on platelets rich plasma for 1 mn, then a dose of 2.5 nm of PAF was added.

The determination is made on a Cronolog Coultronics apparatus which determines the transmission percentage corresponding to the maximum height of the peak before the desaggregation.

The percentage of variation of the inhibition with respect to the transmission percentage is calculated (control: pure DMSO).

This method was described in detail in LABORATORY INVESTIGATIONS, Vol. 41, No. 3, p. 275, 1979, JEAN-PIERRE CAZENAVE, Dr. MED., JACQUES BENVENISTE, DR. MED., AND J. FRASER MUSTARD, M. D., "Aggregation of rabbits platelets by platelet-activating factor is independent of the release reaction and the arachidonate pathway and inhibited by membrane-active drugs".

Results are reported in the following table.

| EXAMPLES | AGGREGATION | | BINDING | |
|---|---|---|---|---|
| | IC50 | (Mol) | IC50 | (Mol) |
| 1 | 1.2 | $10^{-7}$ | 6.2 | $10^{-8}$ |
| 2 | 7.1 | $10^{-7}$ | 2.5 | $10^{-7}$ |
| 3 | 5.6 | $10^{-7}$ | 6.7 | $10^{-7}$ |
| 4 | 1.9 | $10^{-7}$ | 3.2 | $10^{-8}$ |
| 5 | 5.8 | $10^{-6}$ | 6.3 | $10^{-6}$ |
| 6 | 2.4 | $10^{-6}$ | 4.7 | $10^{-6}$ |
| 7 | 4.3 | $10^{-7}$ | 7.4 | $10^{-7}$ |
| 8 | 7.1 | $10^{-8}$ | 3.8 | $10^{-8}$ |
| 9 | 4.1 | $10^{-7}$ | 7.3 | $10^{-7}$ |
| 10 | 5.4 | $10^{-6}$ | 4.1 | $10^{-6}$ |
| 11 | 1.1 | $10^{-8}$ | 3.1 | $10^{-8}$ |
| 12 | 6.2 | $10^{-8}$ | 6.0 | $10^{-8}$ |
| 13 | 3.5 | $10^{-7}$ | 1.4 | $10^{-7}$ |
| 14 | 1.7 | $10^{-7}$ | 4.5 | $10^{-7}$ |
| 15 | 3.7 | $10^{-7}$ | 6.8 | $10^{-7}$ |
| 16 | 2.9 | $10^{-7}$ | 5.3 | $10^{-7}$ |

2. —Passive cutaneous anaphilaxy (rats)

The derivatives according to the invention, when administered at 6.5 and 12.5 mg/kg, by IP route, in rats significantly dose-effect antagonized the passive cutaneous anaphylaxy reaction (local sensibilization induced by injection of homologous immunserum rich in IgE, then immediate hypersensitiveness reaction by systemic injection of the antigen). This protective activity was recovered after oral administration of 25 mg/kg of any of the compounds of the invention (protection varying between 39 and 83% according to the compound).

3. —Immun bronchospasm on guinea-pigs

The compounds of the invention were also studied on the immun bronchospasm induced by antigene injection on a guinea-pig passively conditioned by injection of an heterologous immunserum containg IgE. The 25 mg/kg dose per os of any of the compounds reduces this bronchospasm to 15 to 49% and the 5 mg/kg dose IV to 25% to 53% according to the compound.

We claim:

1. Piperazine derivatives of the general formula I

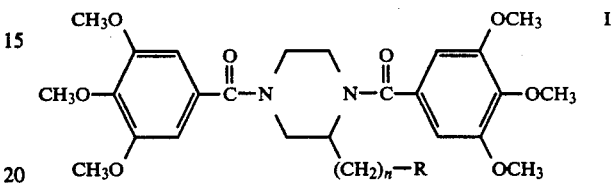

wherein
-$(CH_2)_n$- represents a straight or branched chain alkyl group having from n=1 to n=20 carbon atoms, and
R represents a hydrogen atom, a branched alkyl group, a cycloalkyl group having from 5 to 10 carbon atoms, a phenyl group, optionally substituted by one or several chlorine atoms, methyl or methoxy groups, or straight or branched chain alkenyl groups having from 3 to 11 carbon atoms, and therapeutically acceptable salts thereof.

2. Therapeutic compositions of matter containing an effective amount of at least one compound according to claim 1, associated with the usual carriers for the selected administration route.

* * * * *